(12) United States Patent
Harris et al.

(10) Patent No.: US 8,696,681 B2
(45) Date of Patent: Apr. 15, 2014

(54) ADJUSTABLE INTERBODY INTRODUCER DEVICE AND METHOD

(75) Inventors: Peter M. Harris, Leesburg, VA (US);
Larry E. McClintock, Gore, VA (US);
Todd M. Wallenstein, Asburn, VA (US);
Kevin R. Strauss, Columbia, MD (US)

(73) Assignee: K2M, Inc., Leesburg, VA (US)

( * ) Notice: Subject to any disclaimer, the term of this patent is extended or adjusted under 35 U.S.C. 154(b) by 1801 days.

(21) Appl. No.: 11/529,708

(22) Filed: Sep. 29, 2006

(65) Prior Publication Data

US 2007/0093850 A1     Apr. 26, 2007

Related U.S. Application Data

(60) Provisional application No. 60/721,473, filed on Sep. 29, 2005.

(51) Int. Cl.
*A61B 17/00* (2006.01)

(52) U.S. Cl.
USPC ........................................ 606/99; 623/17.16

(58) Field of Classification Search
USPC ......... 606/246, 279, 86 R, 91, 99, 100, 86 A; 623/17.11, 17.16
See application file for complete search history.

(56) References Cited

U.S. PATENT DOCUMENTS

| | | | | |
|---|---|---|---|---|
| 5,314,429 | A * | 5/1994 | Goble | 606/96 |
| 5,352,231 | A * | 10/1994 | Brumfield et al. | 606/99 |
| 6,592,590 | B2 * | 7/2003 | Simon | 606/99 |
| 6,599,294 | B2 * | 7/2003 | Fuss et al. | 606/99 |
| 7,235,082 | B2 * | 6/2007 | Bartish et al. | 606/99 |
| 7,500,991 | B2 * | 3/2009 | Bartish et al. | 623/17.11 |
| 2001/0021853 | A1 * | 9/2001 | Heckele et al. | 606/99 |
| 2002/0045904 | A1 * | 4/2002 | Fuss et al. | 606/99 |
| 2003/0069586 | A1 * | 4/2003 | Errico et al. | 606/99 |
| 2004/0010261 | A1 * | 1/2004 | Hoag et al. | 606/99 |
| 2004/0024406 | A1 * | 2/2004 | Ralph et al. | 606/90 |
| 2004/0089039 | A1 * | 5/2004 | Russell et al. | 70/278.3 |
| 2004/0117020 | A1 * | 6/2004 | Frey et al. | 623/17.11 |
| 2004/0167534 | A1 * | 8/2004 | Errico et al. | 606/99 |
| 2005/0021042 | A1 * | 1/2005 | Marnay et al. | 606/99 |
| 2005/0055095 | A1 * | 3/2005 | Errico et al. | 623/17.11 |
| 2006/0235426 | A1 * | 10/2006 | Lim et al. | 606/99 |
| 2007/0093850 | A1 * | 4/2007 | Harris et al. | 606/99 |
| 2007/0162128 | A1 * | 7/2007 | DeRidder et al. | 623/17.11 |
| 2007/0173858 | A1 * | 7/2007 | Engh et al. | 606/99 |
| 2007/0198015 | A1 * | 8/2007 | Foley et al. | 606/61 |
| 2007/0260314 | A1 * | 11/2007 | Biyani | 623/17.11 |
| 2008/0221694 | A1 * | 9/2008 | Warnick et al. | 623/17.16 |
| 2008/0306488 | A1 * | 12/2008 | Altarac et al. | 606/99 |
| 2008/0306489 | A1 * | 12/2008 | Altarac et al. | 606/99 |
| 2009/0198246 | A1 * | 8/2009 | Lim et al. | 606/99 |

OTHER PUBLICATIONS

"Universal Joint." The Mirriam-Webster Online Dictionary. Mar. 23, 2009 <http://www.merriam-webster.com/dictionary/laryngoscope>.*

* cited by examiner

*Primary Examiner* — Christian Sevilla
(74) *Attorney, Agent, or Firm* — Carter, DeLuca, Farrell & Schmidt, LLP

(57) ABSTRACT

Provided is a novel surgical instrument having an adjustable distal end that can securely engage an interbody for introduction of the interbody into an intervertebral space, can be adjusted before and during the surgical procedure to vary the angle of the distal end of the device and the angle of introduction of the interbody, and after positioning that interbody at the surgical site, can be easily disengaged and removed.

17 Claims, 7 Drawing Sheets

ADJUSTABLE INTERBODY INTRODUCER DEVICE AND METHOD

BACKGROUND OF THE INVENTION

1. Technical Field

The present invention relates to devices and methods for use in orthopedic spine surgery. In particular, the present invention relates to a device having at least two distinct articulating surfaces, the device being useful as an artificial disc replacement and a method of implanting that device using a posterior approach.

2. Background Art

The human spine is comprised of thirty-three vertebrae at birth and twenty-four as a mature adult. Between each pair of vertebrae is an intervertebral disc, which maintains the space between adjacent vertebrae and acts as a cushion under compressive, bending and rotational loads and motions. A healthy intervertebral disc has a great deal of water in the nucleus pulposus—the center portion of the disc. The water content gives the nucleus a spongy quality and allows it to absorb spinal stress. Excessive pressure or injuries to the disc can cause injury to the annulus—the outer ring that holds the disc together. Generally, the annulus is the first portion of the disc that seems to be injured. These injuries are typically in the form of small tears. These tears heal by scar tissue. The scar tissue is not as strong as normal annulus tissue. Over time, as more scar tissue forms, the annulus becomes weaker. Eventually this can lead to damage of the nucleus pulposus. The nucleus begins to lose its water content due to the damage—it begins to dry up. Because of water loss, the discs lose some of their ability to act as a cushion. This can lead to even more stress on the annulus and still more tears as the cycle repeats itself. As the nucleus loses its water content it collapses, allowing the two vertebrae above and below to move closer to one another. This results in a narrowing of the disc space between the two vertebrae. As this shift occurs, the facet joints located at the back of the spine are forced to shift. This shift changes the way the facet joints work together and can cause problems in the facet joints as well.

When a disc or vertebrae is damaged due to disease or injury standard practice is to remove part or all of the intervertebral disc, insert a natural or artificial disc spacer or interbody and construct an artificial structure to hold the effected vertebrae in place to achieve a spinal fusion.

A major challenge of spine surgery is in the development of surgical instruments for the surgeon to use during the implantation of the devices such as an artificial disc replacement or interbody. The instrumentation must be easy to use, effective, durable and most importantly, must not interfere with or cause further damage to the patient's anatomy.

There is a particular need to provide a specifically designed surgical instrument that can safely be used in the process of implanting a disc spacer or interbody between adjacent vertebrae and then easily disengage the instrument from the implanted interbody.

SUMMARY OF THE DISCLOSURE

The present invention meets the above identified need by providing a novel surgical instrument device that effectively engages an interbody for introduction of the interbody into an intervertebral space and after positioning that interbody can be easily disengaged and removed from the surgical site.

Also provided is a device having an adjustable angle distal end for introducing an interbody into an intervertebral space wherein the distal end of the device is provided with an interbody grasping unit that can securely grasp the interbody for the process of implanting the interbody and, upon completion of the introduction, can be easily disengaged from the implanted interbody.

Also provided is a device having an adjustable angle distal end for introducing an interbody into an intervertebral space wherein the adjustable angle distal portion of the elongated device can be selectively directed to at least one angle away from the longitudinal axis of the device and locked in that configuration.

Also provided is a device having an adjustable angle distal end for introducing an interbody into an intervertebral space wherein the distal portion of the elongated device can be selectively directed to at least one angle away from the longitudinal axis of the device, locked in that configuration, and repeatedly unlocked and readjusted to other angles as required.

Also provided is a method of introducing an interbody into an intervertebral space using a device having an adjustable angle distal end, the distal end being capable of securely connecting to the interbody prior to the implantation of the interbody and easily releasing from the interbody after the interbody is implanted in a subject.

Also provided is a kit containing at least one adjustable angle interbody introducing device as disclosed herein and at least one other orthopedic device or tool used in spine surgery procedures. The kit can include at least one interbody device.

BRIEF DESCRIPTION OF THE DRAWINGS

The foregoing and other features of the adjustable interbody introducer device will become apparent to one skilled in the art to which the present invention relates upon consideration of the following description of exemplary embodiments with reference to the accompanying drawings, wherein.

DETAILED DESCRIPTION OF PREFERRED EMBODIMENTS

Detailed embodiments of the present invention are disclosed herein; however, it is understood that the following description and each of the accompanying figures are provided as being exemplary of the invention, which may be embodied in various forms without departing from the scope of the claimed invention. Thus, the specific structural and functional details provided in the following description are non-limiting, but serve merely as a basis for the invention as defined by the claims provided herewith. The device described below can be modified as needed to conform to further development and improvement of materials without departing from the inventor's concept of the invention as claimed.

Figure 4:
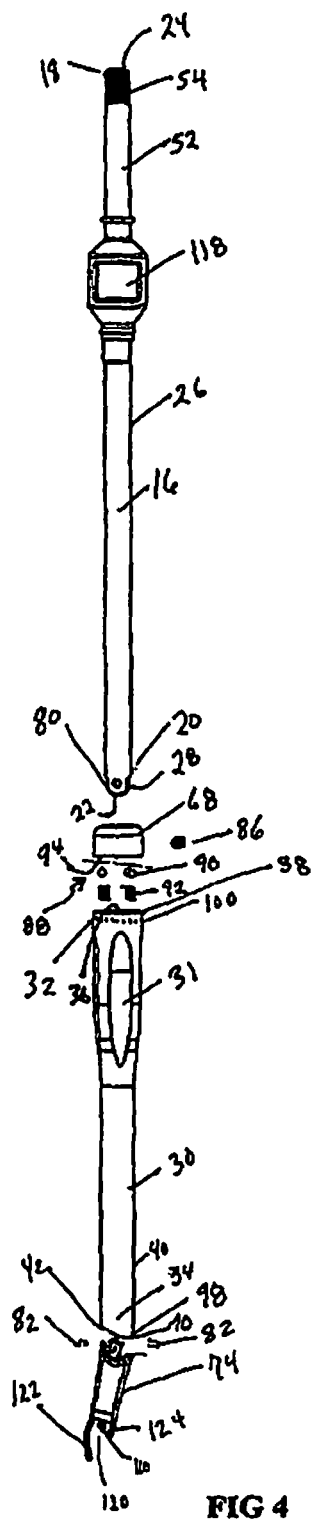
FIG. 4 shows the disassembled components of the device in assembly alignment less the handle and slap hammer connector.

The device, as generally shown at 10 in FIGS. 1, 2A-B, 4, 5 and 8A-C is an interbody introducer having an adjustable angle distal end. The device 10 has a proximal first end 12 and a distal second end 14. As shown in FIG. 4, the device 10 includes a tubular inner shaft 16 having a proximal inner shaft first end 18 and a distal inner shaft second end 20 with an inner shaft lumen 22 extending the full length of the inner shaft 16 and having an inner shaft entry portal 24 defined at the inner shaft first end 18 by the circumferential inner shaft wall 26 and an inner shaft exit portal 28 defined at the inner shaft second end 20 by the circumferential inner shaft wall 26.

As also shown in FIG. 4 the device 10 includes a tubular outer shaft 30 having a proximal outer shaft first end 32 and a distal outer shaft second end 34 with an outer shaft lumen 36 extending the full length of the outer shaft 30 and having an outer shaft entry portal 38 defined at the outer shaft first end 32 by the circumferential outer shaft wall 40 and an outer shaft exit portal 44 defined at the outer shaft second end 34 by the circumferential outer shaft wall 40.

Figure 5:
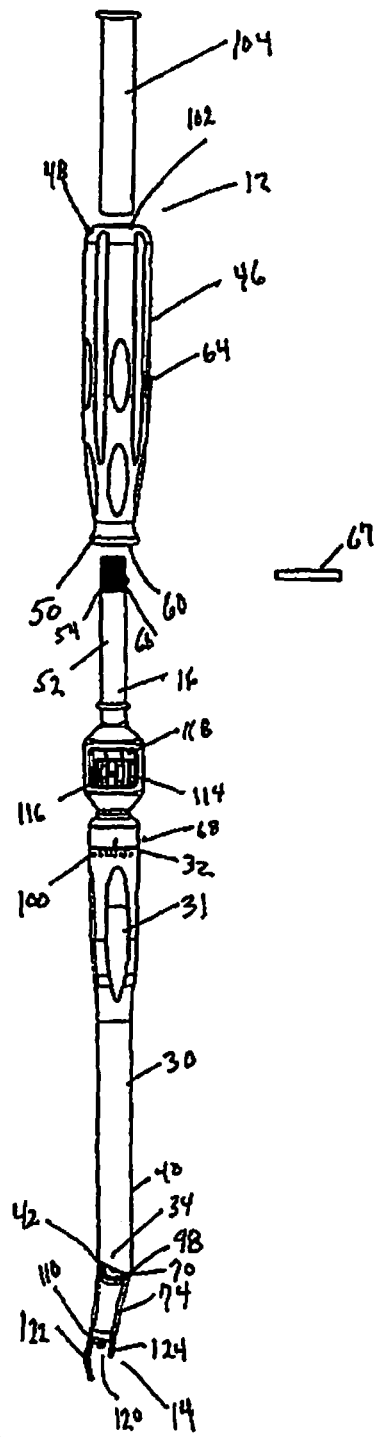
FIG. 5 shows the components of the device, which are shown in FIG. 4, fully assembled with the handle and slap hammer connector in assembly alignment.

The inner shaft 16 is sized and configured to easily fit within the outer shaft 30 so as to permit rotational movement about the longitudinal axis of the device. As shown in FIGS. 1, 2A-B, 5 and 8A-C, the inner shaft 16 is provided with a handle 46 having a handle proximal first end 48 and a handle distal second end 50. The handle 46 is attached around at least a portion of the proximal first end 18 of the inner shaft 16. As shown in FIG. 5 the outer surface 52 of the first end 18 of the inner shaft 16 can be provided with handle attachment threads 54, which are complimentary to handle threads 56, which are defined on at least the distal portion of the inner wall 58 of the handle lumen 60. This threaded attachment of the distal second end 50 of the handle 46 to the proximal first end 18 of the inner shaft 16 is preferred; however, other attachments, as are known in the art can be used without departing from the inventor's concept. Examples of other handle attachments can include, bayonet fittings, snap fittings, cotter pin attachments, and the like. In addition to using a threaded attachment of the handle 46 to the inner shaft 16, the handle 46 and the inner shaft 16 can be provided with complimentary dowel holes 64, 66 and a securing handle dowel pin 67 at or near the location of the threaded attachment.

Movement of the inner shaft 16 within the lumen 36 of the outer shaft 30 is initiated by the manual rotation of handle 46, which is securely connected to the inner shaft 16 so as to directly transfer the rotational movement of the handle 46 to the rotational movement of the inner shaft 16. This rotational movement of the inner shaft 16 within the lumen 36 of the outer shaft 30 effects the adjustment of the relative angle of the distal second end 14 to the longitudinal axis of the device 10 due to the unique articulating interaction of the slant geometry of an outer shaft cam surface 70 at the distal second end 34 of the outer shaft 30 and the geometry of a grasping unit proximal contact surface 72 of the grasping unit 74 of the device 10.

Figure 3:
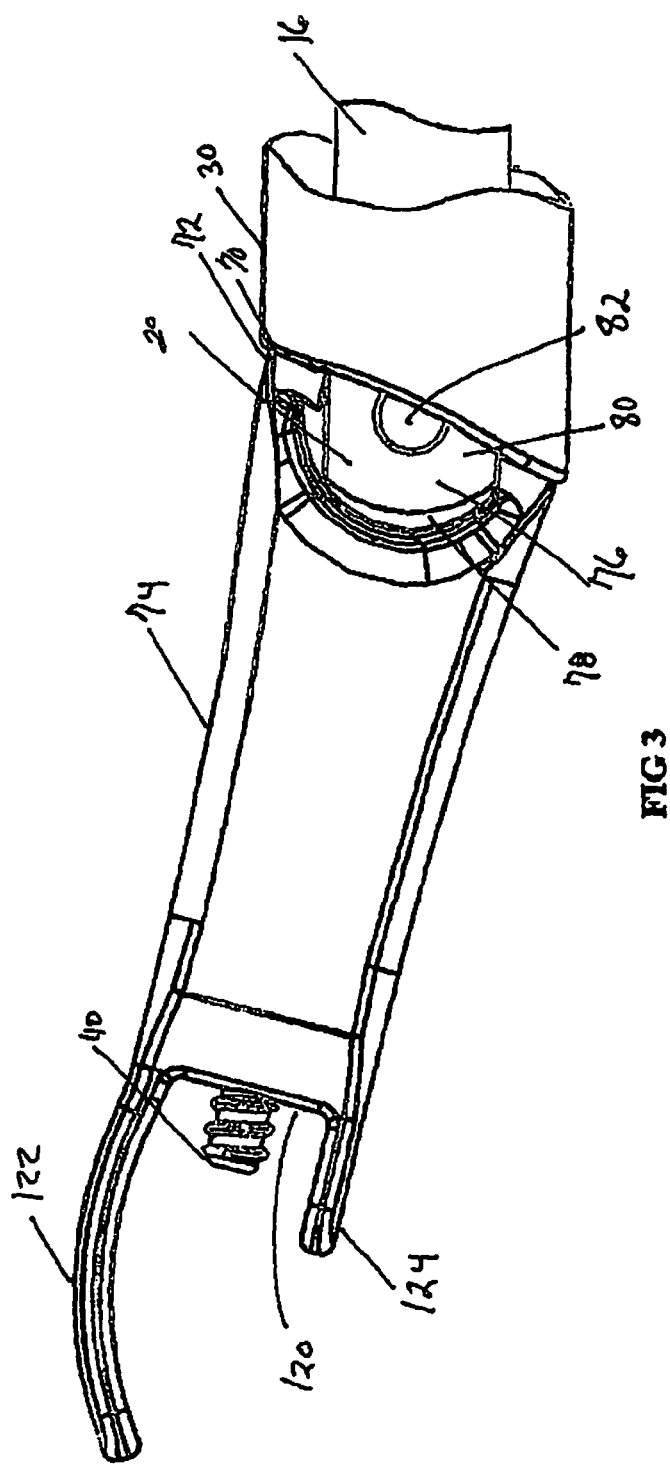
FIG. 3 shows an enlarged detailed view of the interbody grasping unit extending from a truncated representation of the outer shaft and inner shaft of the device.

The grasping unit 74 of the device, as shown in detail in FIG. 3, is connected to the distal second end 20 of the inner shaft 16 by an articulating hinge 76 as shown in FIGS. 1, 2A, 3, 4, 5, 6 and 8A-C. The articulating hinge 76 includes complimentary grasping unit hinge arms 78 that are attached to corresponding inner shaft hinge arms 80 by opposing grasping unit hinge pins 82, 84. The articulating hinge 76 allows movement of the inner shaft 16 and the grasping unit 74 in multiple planes in the same way as is commonly found in a universal type joint, which is well known in the art.

The outer shaft 30 is circumferentially disposed around the at least a portion of the inner shaft 16. The inner shaft 16 is sized and configured to freely rotate within the lumen 36 of the outer shaft 30. The distal second end 34 of the outer housing 30 is approximate to the location of the distal second end 20 of the inner shaft 16. Outer shaft gripping surfaces 31 are provided on the outer shaft to facilitate ease of operation of the device. The proximal first end 32 of the outer shaft 30 is abutted against a proximally disposed angle locking ring 68. As shown in FIG. 4, the locking ring 68 is secured to the inner shaft 16 by a locking ring dowel pin 86. Disposed between the distal inner surface of the locking ring 68 and the surface of the proximal first end 32 of the outer shaft 30 is a biased bearing assembly, generally shown at 88 in FIG. 4. As is well known in the art, the biased bearing assembly 88 includes multiple ball bearing units 90, each bearing 90 having a corresponding biasing element 92, a preferable example of which is a coil spring. As is well known in the art, the components of the assembly 88, under compression from the biasing elements 92, are held in relative position one to the other by the securely affixed locking ring 68. Multiple indentations 94 (not directly shown) that correspond in number, in size and in arc radius to the multiple bearings 90 in the assembly 88 can be defined in the inner surface of the locking ring 68. As is known in the art, operation of the biased bearing assembly 88 requires rotation of the outer shaft 30 around the inner shaft 16, that rotation being punctuated by movement of the biased bearings 90 from one indentation 94 to the next such that the rotational movement is naturally paused as each bearing 90 is biased into the next indentation 94. The tactile feedback of this momentarily interrupted rotation attendant to the biased bearing assembly 88 is similar to a ratcheting effect. In addition to a tactile sensation in the device 10, it is common for biased bearing assemblies to also produce an audible indication of movement of the bearings 90 from one indentation 94 to the next. When the movement is momentarily halted by the user, the biasing elements 92 provide measured resistance to further movement and thus tend to hold the bearings in their respective indentations thereby serving to hold or lock the device 10 in its last selected position.

Figure 1:
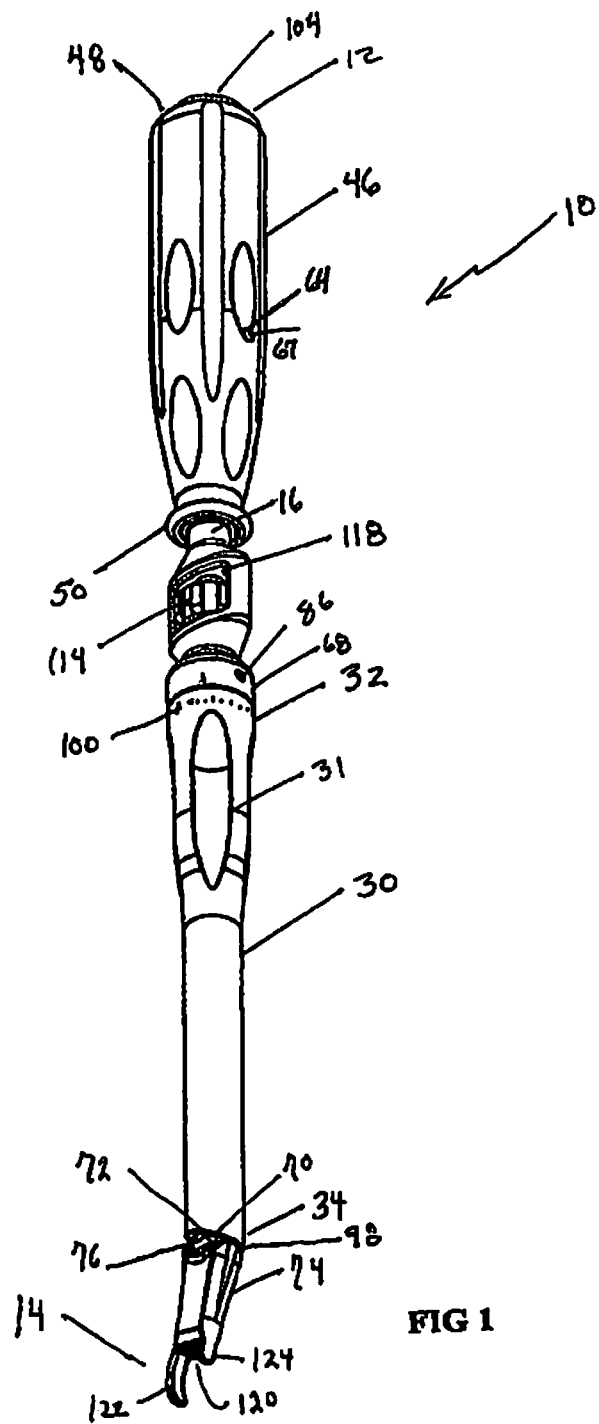
FIG. 1 shows an isometric view of the device having an adjustable angle distal end for introducing an interbody into an intervertebral space. The adjustable angle distal end of the device is shown positioned at an angle that is slightly elevated above the longitudinal axis of the device.
Figure 2A:
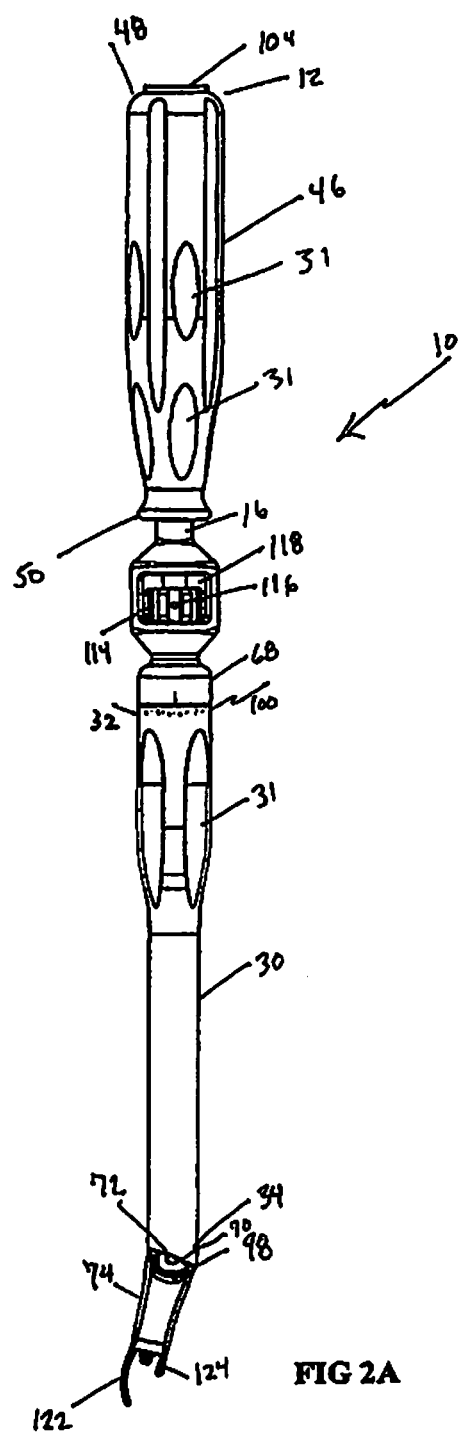
FIGS. 2A-B show a side view and a top view, respectively of the device of FIG. 1.
Figure 2B:
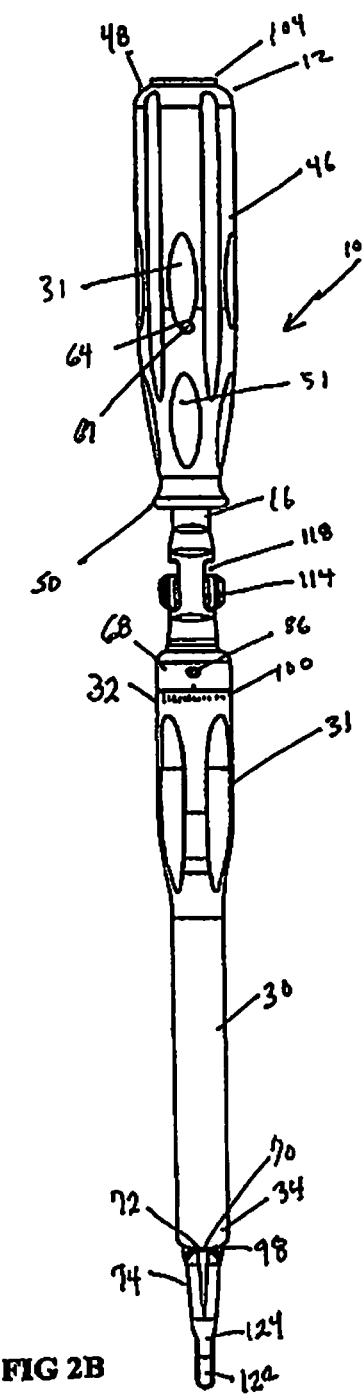
Figure 8A:
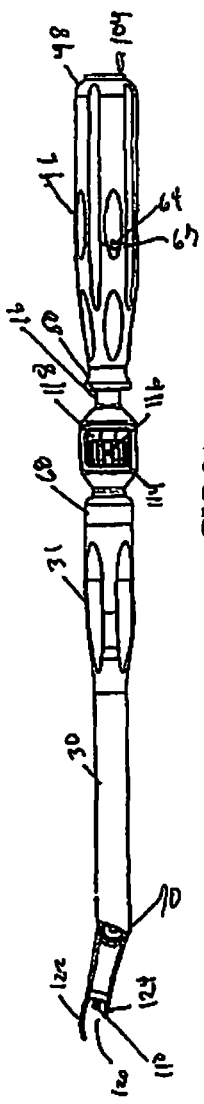
FIGS. 8A-C shows side views of the device having an adjustable angle distal end for introducing an interbody into an intervertebral space, wherein FIGS. 8A, 8B, and 8C, respectively represent only three examples of the multiple angles to which the distal end of the device can be selectively directed.
Figure 8B:
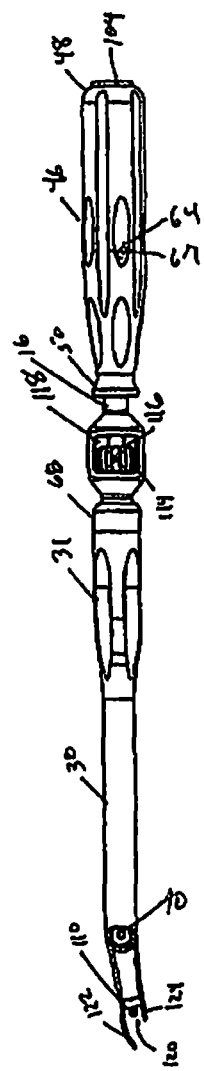
Figure 8C:
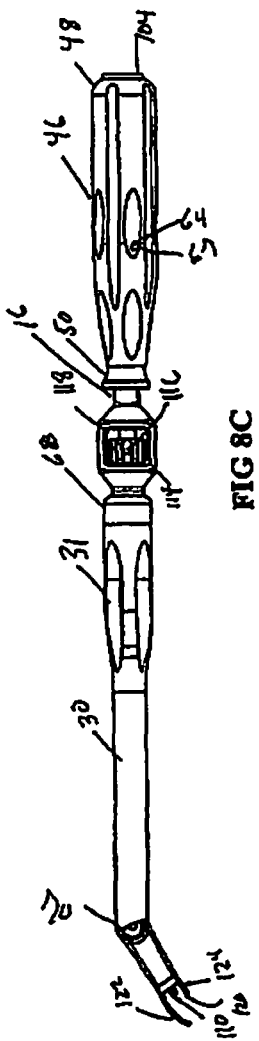

The grasping unit 74 at its proximal edge is provided with a cam surface 96 that is configured to be in contact with the at least a portion of the distal edge 98 of the outer shaft 30 as the inner shaft 16 is selectively rotated within the lumen of the outer shaft 30. As best shown in FIGS. 8A-C, the slant geometry of the distal edge 98 of the outer shaft varies in relative position to the grasping unit 74 cam surface 96 as the inner shaft 16 is rotated. The effect of this contact between the slant geometry of the distal edge 98 and the cam surface 96 of the grasping unit 74 is to alter the angle of the grasping unit 74 relative to the longitudinal axis of the device 10. With reference to the discussion of the halting movement effect that results from rotation of the inner shaft 16 against the bias of the bias bearing assembly 88, it is apparent that as the inner shaft 16 is selectively rotated within the lumen of the outer shaft 30, the angle of the grasping unit 74 will vary in a corresponding and predictable fashion. As the relative rotation progresses, the biased bearing assembly 88 will momentarily halt and lock the angle of the grasping unit in place until additional rotational force is manually applied to the device 10. The user can be provided with tactile and audible feedback of all rotational movement of the device. Further, as shown in FIG. 1, indicia 100 of the degrees of the selected angle can be provided on the proximal portion of the outer surface of the outer shaft. For example, grasping unit angle values indicating the variance from the longitudinal axis of the device 10 of −10 degrees to +50 degrees can be provided. However, the range of possible angles of which the device 10 is capable of achieving is determined by the amount of slant formed along the distal edge 98 of the outer shaft 30 and therefore, the disclosed device 10 can be manufactured to be capable of a wide range of angles.

In operation, the user can employ a driving instrument, such as a surgical hammer or slap hammer to facilitate placement of the interbody into the proper position in the intervertebral space. To facilitate that likely possibility, the handle 46 of the device 10 is provided with a slap hammer recess 102 in the distal end that is sized and configured to accept a slap hammer connector 104 as is shown in FIG. 5. The slap hammer recess 102 can be communicate with and be continuous with the handle lumen 60 so as to provide a through passage along the longitudinal axis of the handle 46.

Figure 6:
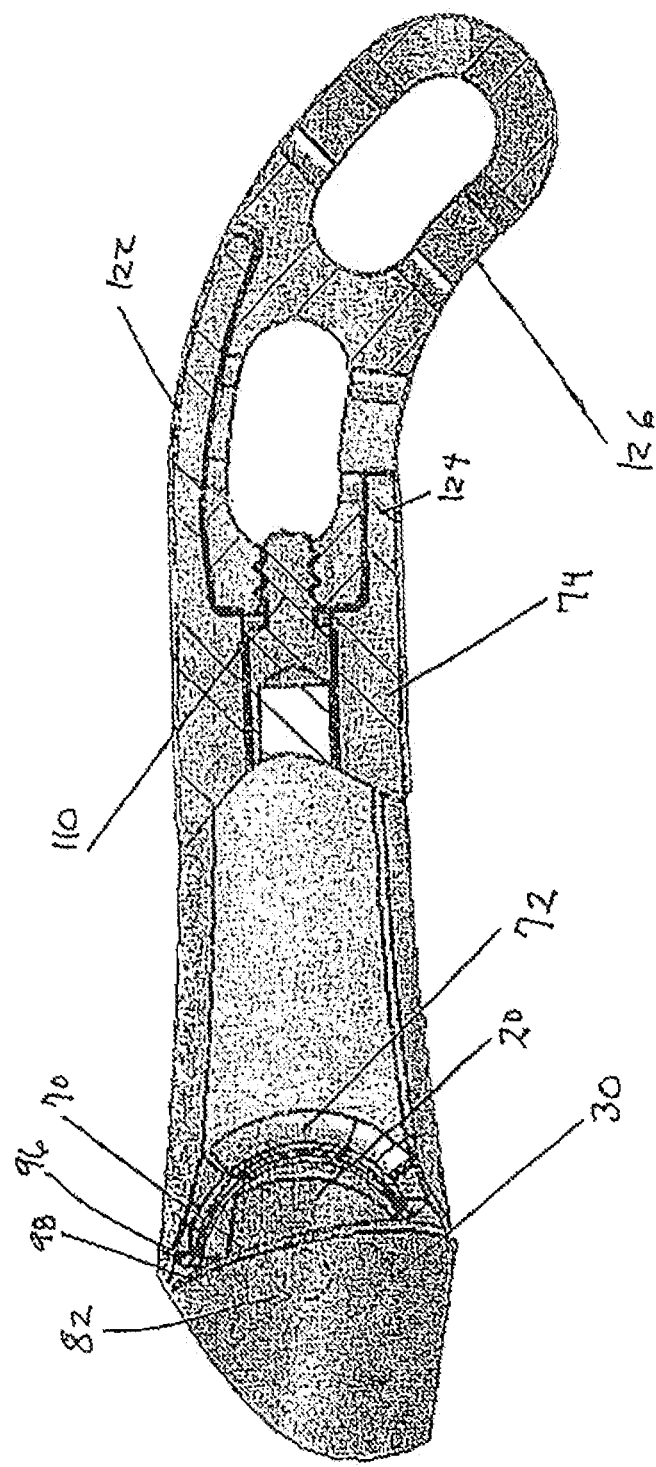
FIG. 6 shows an enlarged cross-sectional side view of the interbody grasping unit extending from a truncated representation of the outer shaft of the device. An interbody device is shown secured in the grasping unit.
Figure 7:
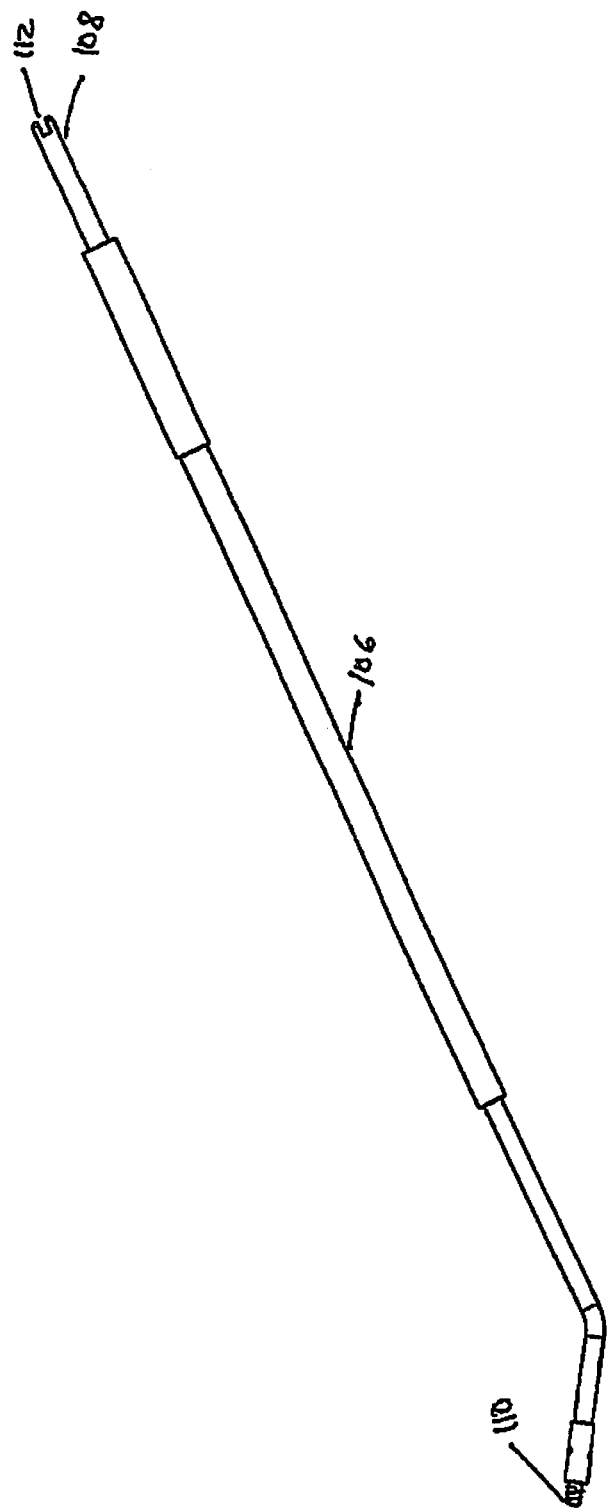
FIG. 7 shows a side view of a threaded interbody connection shaft.

As shown in FIG. 7, an interbody connector shaft 106 within the lumen 22 of the inner shaft 16 is sized and configured to easily rotate around the long axis of the device and translate along the long axis of the device 10. The interbody connector shaft 106 can be manufactured entirely or at least in its most distal portions of materials having good strength but being flexible such that the connector shaft 106 can be repeatedly bent at different angles as shown in FIG. 7. The interbody connector shaft has a connector shaft first end 108 and a connector shaft second end 110. The connector shaft first end 108 is provided with a tool receptacle 112 that preferably corresponds to a standard tool for torque application, such as, for example, a screw driver. The connector shaft second end 110 defines an interbody securing element, which preferably is a threaded protrusion that is sized and configured to correspond to a threaded receptacle defined in the end portion of an interbody, as shown in FIGS. 3, 6, 7 and 8A-C. The connector shaft 106 can be threaded into the interbody as shown in FIG. 6 by attaching a tool, such as a screw driver, to the tool receptacle 112 and apply torque at the first end 108 of the connector shaft 106. Access to the connector shaft tool receptacle 112 within the lumen of the inner shaft 16 can be achieved through the handle lumen 60. Alternatively, as shown in FIGS. 1, 2A-B, 5 and 8A-C, rotational force can also be applied to the interbody connector shaft 106 by manually turning a thumb wheel 114 that can be securely fixed to the interbody connector shaft 106 by a thumb wheel dowel pin 116. Visual and manual access to the thumb wheel 114 is provide through a thumb wheel window 118 defined through a portion of the wall of the inner shaft 16. As shown in FIGS. 2, 4, 5 and 8A-C the thumb wheel window 118 can preferably be defined through opposing sides of the inner shaft 16 so as to expose opposite sides of the thumb wheel 114 and thereby optimize the user's access to the thumb wheel 114.

In the exemplary embodiment described herein, the grasping unit 74 is specifically configured to grasp an interbody implanted in a Transforaminal Lumbar Interbody Fusion (TLIF). As such, the grasping unit is provided with an interbody seat 120 having a specific geometry to correspond to the shape of the interbody. In addition to the threaded portion of the connector shaft second end 110, which is best shown in FIGS. 3 and 6, the interbody seat 120 can be provided with a superior arm 122 and an inferior arm 124 that can be configured to provide circumferential grasping of at least a portion of the interbody 126.

While the device is described herein as an example adapted for use as an adjustable interbody introducer and particularly is well suited for use in Transforaminal Lumbar Interbody Fusion (TLIF), it is within the inventors' understanding that the grasping element can be configured and adapted to conform to any implantable surgical device.

In use, a surgeon can employ the disclosed advice by securing the interbody 126 to the grasping unit 74 of the device 10, making an incision in the subject, defining an approach path to the surgical site, preparing the intervertebral space to receive the interbody 126, and inserting the interbody 126 by adjusting the angle of the distal end of the device to the desired angle and repeating the insertion efforts as necessary. Upon achieving the proper position for the interbody, releasing the interbody from the grasping unit and removing the device from the surgical site.

The device 10 can be manufactured as integral components by methods known in the art, to include, for example, molding, casting, forming or extruding, and machining processes. The components can be manufactured using materials having sufficient strength, resiliency and biocompatibility as is well known in the art for such devices. By way of example only, suitable materials cam include implant grade metallic materials, such as titanium, cobalt chromium alloys, stainless steel, or other suitable materials for this purpose. Some components of the device can be made from plastics, composite materials, and the like.

It is also within the concept of the present invention to provide a kit, which includes the adjustable interbody introducer disclosed herein. Additionally, a kit can include additional orthopedic devices and instruments; such as for example, bone screws or plates, spinal rods, hooks or links and any instruments or tools associated therewith. Such a kit can be provided with sterile packaging to facilitate opening and immediate use in an operating room.

Each of the embodiments described above are provided for illustrative purposes only and it is within the concept of the present invention to include modifications and varying configurations without departing from the scope of the invention that is limited only by the claims included herewith.

What is claimed is:

1. An adjustable interbody introducer comprising:
    an inner shaft having a through lumen, the inner shaft defining a longitudinal axis,
    an outer shaft having a through lumen, said lumen of the outer shaft being of sufficient diameter to permit said inner shaft to easily rotate within said lumen of said outer shaft, said inner shaft being at least partially disposed within said outer shaft,
    an interbody connector shaft being sized and configured to easily rotate within said lumen of said inner shaft, said interbody connector shaft being at least partially disposed within said inner shaft, said interbody connector shaft having a proximal first end comprising a tool receptacle and having a distal second end, said tool receptacle being accessible to contact by a tool inserted through said inner shaft,
    an interbody grasping unit, configured at one end to securely grasp an interbody and capable of easily disengaging and releasing from said interbody as required and having a second end configured to attach to said second end of said interbody connector shaft, said grasping unit being pivotable with respect to both said inner and outer shafts;

an angled distal end of said outer shaft, said angled distal end being an angle or combination of angles other than a right angle to the longitudinal axis and being in contact with a cam surface of said grasping unit, said inner shaft being rotatable with respect to said outer shaft to move said cam surface along said angled distal end to provide a pivot force to said grasping unit.

2. The device of claim 1, further comprising a thumb wheel fixedly connected to said interbody connector shaft and exposed to visual and manual contact through a thumb wheel window defined in the wall of said inner shaft, wherein manual rotation of said thumb wheel effects manual rotation of said interbody connector shaft.

3. The device of claim 2, wherein said interbody connector shaft terminates at said distal second end as a threaded protrusion sized and configured to attach to a corresponding threaded interbody device.

4. The device of claim 1, further comprising a handle with a distal and proximal end having a through handle lumen passing entirely through said handle from said distal end through said proximal end, said proximal end comprising a slap hammer recess, said handle being connected to a proximal end of said inner shaft.

5. The device of claim 4, further comprising a slap hammer connector sized and configured to fit within said slap hammer recess.

6. The device of claim 1, wherein said grasping unit is connected to said inner shaft by a hinged connection.

7. The device of claim 6, wherein said hinged connection is a universal type joint.

8. The device of claim 1, further comprising a biased bearing assembly, said biased bearing assembly comprising multiple bearings, a corresponding number of biasing elements, and a corresponding number of indentations in the device corresponding to the size and shape of the bearings, said biased bearing assembly being fixedly connected to said inner shaft and being in biased forced rotational contact with a surface portion of said outer shaft.

9. The device of claim 1 in combination with an interbody.

10. The device of claim 9, wherein said interbody is for implantation in transforaminal lumbar interbody fusion.

11. The device of claim 1 further comprising angle indicia inscribed on said outer shaft.

12. The device of claim 11, wherein said indicia include a range of angles of −10 degrees to +50 degrees.

13. A method of introducing an interbody to a surgical site, the method comprising:
providing an interbody introducer, said introducer comprising:
an inner shaft having a through lumen,
an outer shaft having a through lumen, said lumen of the outer shaft being of sufficient diameter to permit said inner shaft to easily rotate within said lumen of said outer shaft, said inner shaft being at least partially disposed within said outer shaft,
an interbody connector shaft being sized and configured to easily rotate within said lumen of said inner shaft, said interbody connector shaft being at least partially disposed within said inner shaft, said interbody connector shaft having a proximal first end comprising a tool receptacle and having a distal second end,
an interbody grasping unit, configured at one end to securely grasp an interbody and capable of easily disengaging and releasing from said interbody as required and having a second end configured to attach to said second end of said interbody connector shaft, said grasping unit being pivotable with respect to both said inner and outer shafts,
an angled distal end of said outer shaft, said angled distal end being an angle or combination of angles other than a right angle to the longitudinal axis and being in contact with a cam surface of said grasping unit, said inner shaft being rotatable with respect to said outer shaft to move said cam surface along said angled distal end to provide a pivot force to said grasping unit;
securing an interbody to the grasping unit,
making an incision in a subject,
defining an approach path to the surgical site,
preparing the intervertebral space to receive the interbody,
inserting the interbody by adjusting an angle of the interbody grasping unit to a desired angle and repeating insertion efforts as necessary,
positioning the interbody as required,
releasing the interbody from the grasping unit and removing the introducer from the surgical site.

14. A kit comprising,
at least one interbody introducer, said introducer comprising:
an inner shaft having a through lumen,
an outer shaft having a through lumen, said lumen of the outer shaft being of sufficient diameter to permit said inner shaft to easily rotate within said lumen of said outer shaft, said inner shaft being at least partially disposed within said outer shaft,
an interbody connector shaft being sized and configured to easily rotate within said lumen of said inner shaft, said interbody connector shaft being at least partially disposed within said inner shaft, said interbody connector shaft having a proximal first end comprising a tool receptacle and having a distal second end,
an interbody grasping unit, configured at one end to securely gasp an interbody and capable of easily disengaging and releasing from said interbody as required and having a second end configured to attach to said second end of said interbody connector shaft, said grasping unit being pivotable with respect to both said inner and outer shafts,
an angled distal end of said outer shaft, said angled distal end being an angle or combination of angles other than a right angle to the longitudinal axis and being in contact with a cam surface of said grasping unit, said inner shaft being rotatable with respect to said outer shaft to move said cam surface along said angled distal end to provide a pivot force to said grasping unit;
and at least one other orthopedic device or tool used in spine surgery procedures.

15. The device of claim 1, wherein said interbody connector shaft is a flexible shaft extending through a center lumen in said grasping unit, said interbody connector shaft being rotatable with respect to said inner shaft, said outer shaft, and said grasping unit regardless of relative position of said grasping unit with respect to both inner and outer shafts.

16. The device of claim 1, further including a flexible connector shaft disposed in said inner shaft.

17. The device of claim 16, wherein said flexible connector shaft includes a distal end configured for releasable engagement with said interbody.

* * * * *